US007943376B2

(12) United States Patent
Weiss et al.

(10) Patent No.: US 7,943,376 B2
(45) Date of Patent: *May 17, 2011

(54) PLATELET DERIVED GROWTH FACTOR (PDGF)-DERIVED NEUROSPHERES DEFINE A NOVEL CLASS OF PROGENITOR CELLS

(75) Inventors: Samuel Weiss, Calgary (CA); Andrew K. Chojnacki, Calgary (CA)

(73) Assignee: Stem Cell Therapuetics Inc., Calgary (CA)

(*) Notice: Subject to any disclaimer, the term of this patent is extended or adjusted under 35 U.S.C. 154(b) by 1177 days.

This patent is subject to a terminal disclaimer.

(21) Appl. No.: 10/131,230

(22) Filed: Apr. 25, 2002

(65) Prior Publication Data

US 2002/0197238 A1    Dec. 26, 2002

Related U.S. Application Data

(60) Provisional application No. 60/287,214, filed on Apr. 27, 2001, provisional application No. 60/307,070, filed on Jul. 20, 2001.

(51) Int. Cl.
*C12N 5/0735* (2010.01)
*C12N 5/0797* (2010.01)
(52) U.S. Cl. .................. 435/368; 435/366; 435/377
(58) Field of Classification Search .................. 435/377, 435/368, 375, 384
See application file for complete search history.

(56) References Cited

U.S. PATENT DOCUMENTS

| 5,750,376 A | 5/1998 | Weiss et al. |
| 5,753,506 A | 5/1998 | Johe |
| 5,851,832 A | 12/1998 | Weiss et al. |
| 5,980,885 A | 11/1999 | Weiss et al. |
| 6,040,180 A | 3/2000 | Johe |
| 2002/0098584 A1 | 7/2002 | Palmer et al. |
| 2003/0203844 A1 | 10/2003 | Delfani et al. |
| 2007/0009491 A1 | 1/2007 | Weiss et al. |

FOREIGN PATENT DOCUMENTS

| WO | WO99/11758 | 3/1999 |
| WO | WO 01 88104 | 11/2001 |
| WO | WO 02 088330 | 11/2002 |

OTHER PUBLICATIONS

R. and Bloemers, H., "Signals controlling the expression of PDGF", *Mol. Biology Reports* 22:1-24 (1996).
Ek, B., Westermark, B., Wasteson, A., and Heldin, C.H., "Stimulation of tyrosine-specific phosphorylation by platelet-derived growth factor", *Nature* 295(5848):419-420 (1982).
Hannink, M. and Donoghue, D.J., "Structure and function of platelet-derived growth factor (PDGF) and related proteins", *Biochim Biophys Acta.* 989(1):1-10 (1989).
Kondo, T., et al., "Oligodendrocyte Precursor Cells Reprogrammed to Become Multipotential CNS Stem Cells", *Science*, 289:1754-1757 (2000).
Nishimura, J., Huang, J.S., and Deuel, T.F., "Platelet-derived growth factor stimulates tyrosine-specific protein kinase activity in Swiss mouse 3T3 cell membranes", *Proc Natl Acad Sci U.S.A.* 79(14):4303-4307 (1982).
Rogister, B. et al., "From neural stem cells to myelinating oilgodendrocytes", *Molecular and Cellular Neuroscience*, 14(4-5):287-300 (1999).
Forsberg-Nilsson K, et al., "Platelet-Derived Growth Factor Induces Chemotaxis of Neuroepithelial Stem Cells", *J. Neuroscience Research*, 53(5):521-530 (1998).
Marmur, R. et al., "Isolation and development characterization of cerebral cortical multipotent progenitors", *Developmental Biology*, 204(2):577-591 (1998).
Chojnacki and Weiss, "Platelet derived growth factor (PDGF)—derived neurospheres from the embryonic basal forebrain define a novel class of progenitor cells", *Society for Neuroscience Abstracts*, 27(1):348, (2001).
Erlandsson A, et al., "Inunatrue neurons from CNS stem cells proliferate in response to platelet-derived growth factor", *J. of Neurscience*, 21(10):3483-3491 (2001).
Bogler et al., "Cooperation Between Two Growth Factors Promotes Extended Self-Renewal and Inhibits Differentiation of Oligodendrocyte-Type-2 Astocyte 0-2A Progenitor Cells," Proc. of the Nat. Acad. Sci. USA, 87(16):6368-6372 (1990).
McKinnon et al., "FGF Modulates the PDGF-Driven Pathway of Oligodendrocyte Development," Neuron, 5(5):603-614 (1990).
Nishiyama et al., "Co-localization of NG2 proteoglycan and PDGF alpha-receptor on 02A progenitor cells in the developing rat brain," J. Neurosci. Res., 43(3):299-314 (1996).
Tang et al., "Long-term Culture of Purified Postnatal Oligodendrocyte Precursor Cells: Evidence for an Intrinsic Maturation Program That Plays Out Over Months," J. Cell Bio., 148(5):971-984 (2000).
Cua et al., "Matrix metalloproteinases degrade chondroitin sulfate proteoglycans and promote neurite outgrowth," *The Canadian endMS Research Conference*, Calgary, CA, Dec. 10-13, 2007.
Chojnacki et al., "Distinctions between embryonic and adult human PDGF-responsive neural precursors," *The Canadian endMS Research Conference*, Calgary, CA, Dec. 10-13, 2007. Chojnacki, A. K. and Weiss S., "Platelet derived growth factor (PGDF)-derived neuroshperes from the embryonic basal forebrain define a novel class of progenitor cells". Society for Neuroscience Abstracts 2001, vol. 27, No. 1, p. 348. (Abstract) BIOSIS [online] [retrieved on Mar. 9, 2006]. Retrieved from: STN International, Columbus, Ohio, USA. Accession No. 2001-486863.
Chojnacki, A. K. and Weiss S., "Isolation of a Novel Platelet-Derived Growth Factor-Responsive Precusor from the Embryonic Ventral Forebrain". J Neurosci., Dec. 2004, No. 48, p. 10888-10899.

(Continued)

*Primary Examiner* — Lorraine Spector
*Assistant Examiner* — Stacey MacFarlane
(74) *Attorney, Agent, or Firm* — McKeon Meunier Carlin Curfman

(57) ABSTRACT

The present invention is related to the discovery of a novel class of neural progenitor cells, which proliferate in response to platelet derived growth factor (PDGF) and differentiate into neurons and oligodendrocytes but not astrocytes. Progeny of the progenitor cells can be obtained by culturing brain tissue in PDGF without serum, epidermal growth factor (EGF), fibroblast growth factor 2, or transforming growth factor alpha. Upon subculturing into EGF-containing media, these progeny cells can proliferate and form neurospheres, whereas PDGF has no such effect.

9 Claims, No Drawings

OTHER PUBLICATIONS

Reynolds, B.A. et al., "A Multiponent EGF-Responsive Striatal Embryonic Progenitor Cell Produces Neurons and Astrocytes". J of Neuro., Nov. 1992, vol. 12, No. 10, p. 4565-4574.

Mohapel P., et al. "Platelet-derived growth factor (PDGF-BB) and brain-derived neurotrophic factor (BDNF) induce striatal neurogenesis in adult rats with 6-hydroxydopamine lesions." Neurosci. 132 (2005) 767-776.

Valenzuela, C.F. et al. "Roles of platelet-derived growth factor in the developing and mature nervous systems." Brain Res. Rev. 24 (1997) 77-89.

Chojnacki et al, "Distinctions between fetal and adult human platelet-derived growth factor-responsive neural precursors," Annals of Neurology 64(2):127-42 (2008).

Johe, K.K. et al., "Single factors direct the differentiation of stem cells from the fetal and adult central nervous system." Development vol. 10, pp. 3129-3140, (1996).

PLATELET DERIVED GROWTH FACTOR (PDGF)-DERIVED NEUROSPHERES DEFINE A NOVEL CLASS OF PROGENITOR CELLS

RELATED APPLICATION

This application claims the benefit of U.S. Provisional Application Serial No. 60/287,214, filed Apr. 27, 2001, and U.S. Provisional Application Serial No. 60/307,070 filed Jul. 20, 2001, both of which are hereby incorporated by reference in their entirety.

FIELD OF THE INVENTION

The present invention is related to the discovery of a novel class of neural progenitor cells which can differentiate into neurons and oligodendrocytes but not astrocytes, and methods of proliferating these progenitor cells by using platelet derived growth factor (PDGF).

REFERENCES

U.S. Pat. No. 5,750,376.
U.S. Pat. No. 5,980,885.
U.S. Pat. No. 5,851,832.
Dirks R and Bloemers H. 1996. Signals controlling the expression of PDGF. Mol. Biology Reports 22: 1-24.
Ek B, Westermark B, Wasteson A, and Heldin C H. 1982. Stimulation of tyrosine-specific phosphorylation by platelet-derived growth factor. Nature 295(5848):419-420.
Hannink M and Donoghue D J. 1989. Structure and function of platelet-derived growth factor (PDGF) and related proteins. Biochim Biophys Acta. 989(1): 1-10.
Nishimura J, Huang J S, and Deuel T F. 1982. Platelet-derived growth factor stimulates tyrosine-specific protein kinase activity in Swiss mouse 3T3 cell membranes Proc Natl Acad Sci U S A. 79(14):4303-4307.

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

The development of the neural system has been an intensively studied area. For example, neurodegenerative disease has become an important concern due to the expanding elderly population which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the central nervous system (CNS), leading to inability of these cells or the brain region to carry out their intended function. Therefore, it is desirable to find out how neural cells, including neurons, oligodendrocytes and astrocytes, are generated. With such findings, neural cells can then be produced in vivo or in vitro to compensate for the degenerate or injured neural cells.

A major progress in this study was the discovery of multipotent neural stem cells (for example see U.S. Pat. Nos. 5,750,376; 5,980,885; 5,851,832). Briefly, these stem cells may be isolated from both fetal and adult brains, and cultured in vitro indefinitely. These cells retain the ability to proliferate in response to growth factors, or differentiate into all lineages of neural cells (neurons and glia cells, including astrocytes and oligodendrocytes) in response to differentiation stimuli. To date, epidermal growth factor (EGF), transforming growth factor alpha (TGF-α) and fibroblast growth factor-2 (FGF-2) are the only factors known to induce the proliferation of single precursor cells that can give rise to neurons, oligodendrocytes, and astrocytes. However, the role of other regulatory factors or cells in the development of the neural system remains to be uncovered.

SUMMARY OF THE INVENTION

The present invention relates to the discovery of a novel class of progenitor cells which can proliferate from brain tissue in the presence of platelet derived growth factor (PDGF). Epidermal growth factor (EGF), transforming growth factor alpha (TGF-α) or fibroblast growth factor-2 (FGF-2) are not required. The progeny of these progenitor cells are capable of differentiating into neurons and oligodendrocytes, but not astrocytes. In addition, while these progeny cells can self-renew and expand when subcultured into media containing EGF, they do not proliferate in response to PDGF. Therefore, these cells are a novel class of progenitor cells.

Accordingly, one aspect of the present invention provides a method of producing progeny of a neural progenitor cell wherein the progenitor cell is capable of differentiating into neurons and oligodendrocytes but not astrocytes, comprising culturing brain tissue in the presence of platelet derived growth factor (PDGF) under conditions that allow proliferation of said progenitor cell.

In a preferred embodiment of the present invention, the progeny cells are capable of proliferating in response to epidermal growth factor (EGF) but not PDGF.

Preferably, the brain tissue is cultured in the absence of serum, EGF, fibroblast growth factor 2 (FGF-2), transforming growth factor alpha (TGF-α), or any combination thereof. The brain tissue may be obtained from embryonic or adult brains. When the tissue is obtained from embryonic brains, it is preferably from the ganglionic eminence and more preferably from medial ganglionic eminence.

Also provided are the progeny cells produced by culturing brain tissue in the presence of PDGF as described above.

Another aspect of the present invention provides a method of screening drugs, comprising:
(a) providing a population of the progeny cells of the present invention;
(b) contacting the progeny cells with a candidate drug; and
(c) determining the effect of the candidate drug on the progeny cells.

If the candidate drug leads to a desired effect, the drug can be further tested and developed. The desired effect may be, for example, proliferation of the progeny cells, activation or inhibition of an enzyme that is associated with a disease or medical condition, or binding of a receptor in the cell.

Another aspect of the present invention provides a method of identifying genes that are involved in proliferation or differentiation of the progenitor cells, comprising providing a cDNA library prepared from a population of proliferated cells, providing a cDNA library prepared from a population of differentiated cells, and comparing the two cDNA libraries. cDNAs that are present selectively in the proliferated cell library are likely involved in proliferation, while cDNAs that are present selectively in the differentiated cell library are likely involved in differentiation. These cDNAs can then be further characterized according to established methods in the art.

In addition, the present invention also provides a method of identifying genes that participate in astrocyte differentiation, comprising comparing a cDNA library prepared from differentiated multipotent neural stem cells to a cDNA library prepared from differentiated progeny cells of the progenitor cells described herein. Since multipotent neural stem cells differentiate to neurons, oligodendrocytes and astrocytes, while the progeny cells of the present invention differentiate to neurons and oligodendrocytes only, cDNAs present in the neural stem cell library but not the library of the progeny cells will likely participate in astrocyte differentiation. These cDNAs can then be further characterized according to established methods in the art.

Accordingly, also provided are cDNA libraries prepared from the progenitor cells or progeny, as well as nucleic acid or protein microarrays prepared using the nucleic acids or proteins of the progenitor cells and progeny.

Still another aspect of the present invention provides a method of modifying the progeny cells described herein, comprising introducing a nucleic acid into the progeny cells to result in alteration in the genetic material in the cells. The resultant modified cells are also provided.

Yet another aspect of the present invention provides a method of treating or ameliorating a disease or medical condition associated with neuron or oligodendrocyte loss or dysfunction, comprising transplanting an effective amount of the progeny cells to a mammal harboring the disease or medical condition. Optionally, other biological agents can be administered to the mammal as well, including, e.g., EGF, PDGF, FGF-1, FGF-2, TGF-α, TGF-β, nerve growth factor (NGF), ciliary neurotrophic factor (CNTF), brain derived neurotrophic factor (BDNF), neurotrophin 3, nuerotrophin 4, leukemia inhibitory factor (LIF), bone morphogenic protein 2 (BMP-2), insulin-like growth factors, insulin, growth factor, prolactin, interleukins, forskolin, cAMP or cAMP analogs, pituitary adenylate cyclase activating polypeptide (PACAP) phorbol esters, estrogen and ovarian hormones. These biological agents may be administered prior to, concurrently or after transplantation of the progeny cells. The transplanted cells may be syngeneic, allogeneic or xenogeneic to the transplantation recipient. Preferably, the transplant is syngeneic or allogeneic, and most preferably syngeneic.

Another aspect of the present invention provides a method of inducing proliferation of a neural progenitor cell that differentiate into neurons and oligodendrocytes but not astrocytes, comprising administering an effective amount of platelet derived growth factor (PDGF) to a mammal. The PDGF, or an agent known to induce or activate PDGF, can be administered via any route known in the art. PDGF is preferably administered into the brain of the mammal. This method can be combined with the transplantation described above.

Also provided are pharmaceutical compositions comprising progeny cells of the present invention. The pharmaceutical compositions preferably further comprise a pharmaceutically acceptable excipient and/or a pharmaceutically acceptable carrier.

DETAILED DESCRIPTION OF THE INVENTION

The present invention relates to the discovery of a novel class of progenitor cells which are derived from brain tissue and proliferate in the presence of platelet derived growth factor (PDGF) to form neurospheres. These PDGF-generated neurospheres contain progeny cells which are capable of differentiating primarily into neurons and oligodendrocytes. In addition, while these progeny cells can self-renew and expand when subcultured into EGF-containing media, they do not proliferate in response to PDGF.

Prior to describing the invention in further detail, the terms used in this application are defined as follows unless otherwise indicated.

Definition

A "multipotent neural stem cell", or "neural stem cell", is a stem cell in the neural cell lineage. A stem cell is a cell which is capable of reproducing itself. In other words, when a stem cell divides, at least some of the resulting daughter cells are also stem cells. The neural stem cells, and their progeny, are capable of differentiating into all the cell types in the neural cell lineage, including neurons, astrocytes and oligodendrocytes (astrocytes and oligodendrocytes are collectively called glia or glial cells). Therefore, the neural stem cells are multipotent neural stem cells. Multipotent neural stem cells are described, for example, in U.S. Pat. Nos. 5,750,376; 5,980,885; and 5,851,832.

The adult neural stem cells preferably refer to the neural stem cells located in or derived from the subventricular zone (SVZ) of the forebrain of adult mammals, which are different from the proliferating cells in the adult hippocampus.

The "progeny" of the novel progenitor cells described herein refers to any and all cells derived from the progenitor cells as a result of proliferation or differentiation. In particular, the progeny cells include the cells in the primary neurospheres which are prepared by culturing brain tissue in the presence of PDGF but not EGF, FGF-2, or TGF-α.

A "neurosphere" or "sphere", as used herein, is a cluster of cells derived from a single neural cell.

A "platelet derived growth factor", or "PDGF" is a protein factor which (1) shares substantial sequence identity with the native human PDGF; and (2) possesses a biological activity of the native human PDGF. Native PDGF consists of two polypeptide chains selected from Chain A and Chain B. Chain A and Chain B are similar. For example, the human Chain A and Chain B share a 56% sequence identity in the mature PDGF molecule. A PDGF molecule may consist of A-A, A-B or B-B. A discussion of the structural and functional relationship of PDGF can be found, for example, in Hannink et al., 1989.

A protein which shares "substantial sequence identity" with the native human PDGF consists of at least one polypeptide that is at least about 30% identical with Chain A or Chain B of the native human PDGF at the amino acid level. The PDGF is preferably at least about 40%, more preferably at least about 60%, yet more preferably at least about 70%, and most preferably at least about 80% identical with Chain A or Chain B of the native human PDGF at the amino acid level. Thus, the term "PDGF" encompasses PDGF analogs which are the deletional, insertional, or substitutional mutants of the native PDGF. Furthermore, the term "PDGF" encompasses the PDGFs from other species, the naturally occurring variants, and different post-translationally modified forms (such as the glycosylated and phosphorylated forms) thereof.

The phrase "percent identity" or "% identity" with the native PDGF refers to the percentage of amino acid sequence in Chain A or Chain B of the native human PDGF which are also found in the PDGF analog when the two sequences are best aligned (including gaps). Percent identity can be determined by any methods or algorithms established in the art, such as LALIGN or BLAST.

A factor possesses a "biological activity of PDGF" if it is capable of binding to any known PDGF receptor and stimulates the tyrosine kinase activity of the receptor (Ek et al., 1982; Nishimura et al., 1982).

A "PDGF-derived neurosphere" or "PDGF-generated neurosphere" is a neurosphere produced from brain tissue in the presence of PDGF. These neurospheres are primary neurospheres since they are generated from brain tissue without cell passaging.

An "EGF-derived neurosphere" or "EGF-generated neurosphere" is a neurosphere produced from brain tissue in the presence of EGF. These neurospheres are primary neurospheres since they are generated from brain tissue without cell passaging.

A "secondary neurosphere" is a neurosphere generated by dissociating (passaging) a primary neurosphere and culturing the dissociated cells under conditions which result in the formation of neurospheres from single cells.

A "neural disease or condition associated with neuron or oligodendrocyte loss or dysfunction" is a disease or medical condition that is caused by or otherwise associated with neuron/oligodendrocyte loss or dysfunction. Examples of these diseases or conditions include neurodegenerative diseases, brain injuries or CNS dysfunctions. Neurodegenerative diseases include, for example, Alzheimer's Disease, multiple sclerosis (MS), macular degeneration, glaucoma, diabetic retinopathy, peripheral neuropathy, Huntington's Disease, amyotrophic lateral sclerosis, and Parkinson's Disease. Brain injuries include, for example, stroke (e.g., hemorrhagic stroke, focal ischemic stroke or global ischemic stroke) and traumatic brain injuries (e.g. injuries caused by a brain surgery or physical accidents). CNS dysfunctions include, for example, depression, epilepsy, neurosis and psychosis.

"Treating or ameliorating" means the reduction or complete removal of the symptoms of a disease or medical condition.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Methods

Fibroblast growth factor-2, transforming growth factor a, and epidermal growth factor can induce the in vitro proliferation of multipotent neural stem cells, derived from the E14 mouse basal forebrain or adult brain tissue, into neurospheres of undifferentiated cells. To date, these are the only factors which have been reported to induce the proliferation of single precursor cells that can give rise to neurons, oligodendrocytes, and astrocytes.

In the present invention, we investigated if PDGF alone could stimulate the formation of neurospheres in defined media. As shown in Example 1, PDGF induces the formation of neurospheres from dissociated cells of the E14 mouse basal forebrain in the absence of EGF, TGF-α, and FGF-2. The formation of these neurospheres was inhibited by Tyrphostin AG 1296, an inhibitor of PDGF receptor phosphorylation, indicating that PDGF-derived neurosphere formation is mediated by PDGF receptor kinase action (Example 2).

The PDGF-generated neurospheres consist of cells that are different from EGF-generated neurospheres. When primary brain tissue culture is exposed to EGF, multipotent neural stem cells proliferate and form neurospheres. As shown in Example 4, these primary neurospheres can be dissociated into single cells, cultured under clonal conditions in the presence of EGF or PDGF, and expand to form secondary neurospheres. In contrast, when PDGF-generated neurospheres were dissociated, the constituent cells could not self-renew or produce secondary neurospheres when subcultured back into PDGF. However, PDGF-generated neurospheres did self-renew/expand when subcultured into EGF (Example 3).

The differentiation patterns of PDGF- and EGF-derived neurospheres are also different. Primary PDGF-generated neurospheres differentiate primarily into neurons and oligodendrocytes (Example 5), as opposed to the neurospheres derived from multipotent neural stem cells that differentiate into neurons, oligodendrocytes and astrocytes, wherein the percentage of astrocyte is typically 60-70%.

Consistent with the results described above, further evidence indicates that the EGF-generated neurospheres and PDGF-generated neurospheres are produced from cells with different spatial distribution patterns. As shown in Example 6, ganglionic eminence from E14 embryos was dissected into two portions, medial ganglionic eminence (MGE) and lateral ganglionic eminence (LGE). MGE and LGE were then dissociated, cultured in either EGF or PDGF, and allowed to form neurospheres. In the presence of PDGF, neurospheres were produced primarily from MGE-derived cells, with LGE producing very few neurospheres. However, both MGE and LGE were capable of efficiently producing neurospheres in the presence of EGF. These results thus indicate that the EGF-generated spheres and PDGF-generated spheres do not come from the same cells.

Furthermore, we also discovered that when both EGF and PDGF are present in the culture media, more neurospheres are produced than with either EGF or PDGF alone. Although there are several possible explanations for this observation, the result is again consistent with the notion that PDGF induces the formation of neurospheres from a novel progenitor cell, which is not the multipotent neural stem cell.

The present invention thus provides a method of producing progeny of a novel class of progenitor cells, which, in response to PDGF, proliferate to neurospheres with unique proliferation and differentiation properties. These neurospheres can be obtained by culturing brain tissue in defined media in the absence of EGF, TGF-α, FGF-2, serum or any combination thereof. The brain tissue can be derived from any mammalian brain, including adult and embryonic brains. Preferably, the brain tissue is harvested from the forebrain, particularly the striatum. The brain tissue is more preferably ganglionic eminence, and most preferably medial ganglionic eminence. The brain tissue is preferably from a primate, rodent, feline, canine, domestic livestock (such as cattle), particularly human.

These progenitor cells, as well as their progeny, can be used to produce neurons and oligodendrocytes. Since multipotent neural stem cells typically produce about 60-70% astrocytes, the progenitor cells of the present invention provide a more enriched source for neurons and oligodendrocytes. As such, the progenitor cells and their progeny can be used to treat or ameliorate neural diseases or conditions associated with neuron or oligodendrocyte loss or dysfunction, such as Alzheimer's Disease, multiple sclerosis (MS), macular degeneration, glaucoma, diabetic retinopathy, peripheral neuropathy, Huntington's Disease, amyotrophic lateral sclerosis, Parkinson's Disease, stroke (e.g., hemorrhagic stroke, focal ischemic stroke or global ischemic stroke), traumatic brain injuries (e.g. injuries caused by a brain surgery or physical accidents), depression, epilepsy, neurosis and psychosis.

The progenitor cells and their progeny can be cultured in vitro and transplanted into a mammal to compensate for lost neurons or oligodendrocytes. In this treatment, the progeny may be neurons and oligodendrocytes that have been induced to differentiate in vitro, or precursor cells from PDGF-derived neurospheres. Growth factors or other biological agents can be co-administered into the mammal to facilitate proliferation and/or differentiation of neural cells. These growth factors and biological agents include, but are not limited to, EGF, PDGF, FGF-1, FGF-2, TGF-α, TGF-β, nerve growth factor (NGF), ciliary neurotrophic factor (CNTF), brain derived neurotrophic factor (BDNF), neurotrophin 3, nuerotrophin 4, leukemia inhibitory factor (LIF), bone morphogenic protein 2 (BMP-2), insulin-like growth factors, insulin, growth factor, prolactin, interleukins, forskolin, cAMP or cAMP analogs, pituitary adenylate cyclase activating polypeptide (PACAP) phorbol esters, estrogen and ovarian hormones. It is also contemplated that other cells, such as multipotent neural stem cells, can be transplanted into the same mammal to provide additional source of neural cell. These other cells, growth factors or biological agents can be given to the mammal prior to, concurrently with, or after transplantation of the progenitor cells and progeny of the present invention.

Alternatively, PDGF can be administered in vivo to induce proliferation of the progenitor cells and ultimately compensate for lost neurons and/or oligodendrocytes. PDGF, or agents known to induce or activate PDGF, can be administered by any route. PDGF is preferably administered into the brain, more preferably a ventricle in the brain and most preferably the lateral ventricle. Any agents known to induce or activate PDGF can also be used (e.g., see Dirks et al., 1996). Growth factors and/or other biological agents, as described above, can optionally be administered prior to, concurrently with, or after administration of PDGF.

The novel progenitor cells and their progeny can also be used to identify genes that are involved in proliferation or differentiation of these cells. For example, a cDNA library can be prepared using the neurospheres produced by culturing brain tissue in PDGF as disclosed herein. The neurospheres are then exposed to biological agents that induce the spheres to proliferate or differentiate, and another cDNA library is prepared using the proliferated or differentiated cells. By comparing the two cDNA libraries (e.g., by subtraction cloning), genes that participate in proliferation or differentiation can be identified. Those genes that are up-regulated in the process of proliferation may include, without being limited to, genes encoding transcription factors, enzymes and growth factor receptors that stimulate proliferation or inhibit differentiation. The genes that are down-regulated during proliferation may include, without being limited to, gene encoding transcription factors, enzymes and growth factor receptors that inhibit proliferation or induce differentiation to neurons and/or oligodendrocytes. Similarly, the genes that are up-regulated in the process of differentiation may include, without being limited to, genes encoding transcription factors, enzymes and growth factor receptors that inhibit proliferation or stimulate differentiation to neurons and/or oligodendrocytes. The genes that are down-regulated during differentiation may include, without being limited to, gene encoding transcription factors, enzymes and growth factor receptors that induce proliferation or inhibit differentiation to neurons and/or oligodendrocytes.

Since the progenitor cells of the present invention do not differentiate to astrocytes and multipotent neural stem cells do, the present invention also provides a method of identifying factors or genes that control astrocyte formation. For example, the cDNA library of differentiating neural stem cells may be subtracted with the cDNA library of proliferating neural stem cells to remove proliferation-related genes and house-keeping genes. Thereafter, the subtracted library can be further subtracted with the cDNA library prepared from cells of the present invention that have been induced to differentiate. Differentiating factors that are selective for astrocytes should remain, while other differentiating factors are likely to be removed by this second subtraction.

The progenitor cells and progeny can also be used to identify potential therapeutic agents for diseases. For example, the cells can be exposed to various candidate drugs and the effect of the candidates determined. Depending on the purpose of the drug screening, the practitioner may look for, for instance, the expression of certain neural marker, the alteration of activity level of an enzyme, the formation of a specialized cell type, or increased cell numbers. Candidate drugs that result in the desired effect can then be further tested and developed.

It should be noted that the progeny cells of the present invention can be modified by genetic engineering. The modified cells can then be transplanted into a mammal or used to study neurobiology. The methods of modification and nucleic acids to be used in such modification will vary depending on the purpose of the modification. For example, the cells may be modified to produce a biological agent, to knock out a gene, or to express a reporter gene that can be used to detect the effect of candidate drugs in a drug screening system. The methods and nucleic acids to be used can be determined by people of ordinary skill according to the disclosure herein and knowledge in the art.

Compositions

The present invention provides a progenitor cell that responds to PDGF to form neurospheres in the absence of EGF, FGF-2, TGF-α, serum, and the combination thereof. Also provided are neurospheres obtained as described above, which comprise progeny cells of the progenitor. The progeny can differentiate to neurons and oligodendrocytes but not astrocytes. cDNA libraries and microarrays containing the nucleic acids or proteins of the progeny cells are also provided, as well as progeny cells that have been modified by genetic engineering techniques.

The present invention further provides pharmaceutical compositions comprising the progenitor cells, or particularly the progeny cells, of the present invention. These pharmaceutical compositions are useful, for example, in transplantation treatment for subjects with a disease or condition associated with neuron or oligodendrocyte loss or dysfunction. The pharmaceutical compositions preferably further comprise a pharmaceutically acceptable excipient and/or a pharmaceutically acceptable carrier.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| ° C. = | degree Celsius |
| hr = | hour |
| min = | minute |
| µM = | micromolar |
| mM = | millimolar |
| M = | molar |
| ml = | milliliter |
| µl = | microliter |
| mg = | milligram |
| µg = | microgram |

-continued

| | |
|---|---|
| FBS = | fetal bovine serum |
| DTT = | dithiothrietol |
| SDS = | sodium dodecyl sulfate |
| PBS = | phosphate buffered saline |
| DMEM = | Dulbecco's modified Eagle's medium |
| α-MEM = | α-modified Eagle's medium |
| β-ME = | β-mercaptoethanol |
| EGF = | epidermal growth factor |
| FGF = | fibroblast growth factor |
| PDGF = | platelet derived growth factor |
| TGF-α = | transforming growth factor alpha |
| DMSO = | dimethylsulfoxide |
| MGE = | medial ganglionic eminence |
| LGE = | lateral ganglionic eminence |

Example 1

PDGF Induces Production of Primary Neurospheres

E14 striatum was mechanically dissociated as previously described (for example see U.S. Pat. Nos. 5,750,376; 5,980,885; or 5,851,832) and plated at 10,000 cells/ml in 6 well plates in defined culture media plus 100 ng/ml of PDGF-AA (Peprotech). The composition of defined culture media is as follows:
DMEM/F12 (1:1)
glucose (0.6%)
glutamine (2 mM)
sodium bicarbonate (3 mM)
HEPES (5 mM)
insulin (25 µg/ml)
transferrin (100 µg/ml)
progesterone (20 nM)
putrescine (60 µM)
selenium chloride (30 nM)

Neurospheres, which are clusters of neural cells derived from single cells, formed after 7 days of culture in vitro (DIV). Six wells per experiment were counted for neurosphere production and the results are shown below:

| Experiment # | Average number of neurospheres produced/well |
|---|---|
| 1 | 14.5 |
| 2 | 9.2 |
| 3 | 34.3* |
| 4 | 8.6 |
| 5 | 7.7 |
| 6 | 32.5* |
| | average = 17.7 ± 5.0 |

*PDGF appears to be approximately 3 fold more potent when used immediately after reconstitution in defined culture media.

In control experiments, wherein PDGF was omitted from the culture media, no neurospheres formed. Therefore, PDGF is capable of inducing neurosphere production from single precursor cells in the absence of serum, EGF, TGF-α and FGF-2.

Example 2

Tyrphostin AG 1296 Inhibits the Production of Primary Neurospheres by Pdgf but Not EGF In order to determine if the PDGF-induced primary neurosphere formation is mediated by the PDGF receptor kinase, a selective PDGF receptor kinase inhibitor, Tyrphostin AG 1296, was added to neurosphere culture. Primary cells were cultured at 10,000 cells/ml in the presence of either EGF or PDGF, plus 5 µM of Tyrphostin AG 1296 (Sigma) or DMSO in the same volume as Tyrphostin (DMSO being the solvent for Tyrphostin). Results are expressed below as the percentage of neurospheres formed, with the number of PDGF- or EGF-derived neurospheres arbitrarily set at 100%, respectively.

TABLE 1

The Effect of Tyrphostin on neurosphere formation in response to EGF or PDGF

| | PDGF or EGF alone | with DMSO | with Tyrphostin |
|---|---|---|---|
| PDGF | 100% | 97% | 10% |
| EGF | 100% | 101% | 55% | n = 3 to 9

Therefore, Tyrphostin AG 1296 almost abolished primary neurosphere formation induced by PDGF, indicating that formation of the PDGF-derived neurospheres is mediated via PDGF receptor kinase action. EGF-derived neurosphere formation was also inhibited by Tyrphostin AG 1296 to some extent. Although the reasons for the inhibition of EGF action are not clear, it is possible that Tyrphostin AG 1296 is also a partial inhibitor for the EGF receptor.

Example 3

PDGF-Derived Primary Neurospheres can be Subcultured into EGF but Not PDGF Containing Media Single PDGF primary neurospheres prepared as described in Example 1 were transferred into 96-well plates and mechanically dissociated in either the presence of 20 ng/ml EGF (Peprotech) or 100 ng/ml PDGF-AA. The formation of secondary neurospheres was assayed after 7 or more days in culture in vitro. The results are shown below.

| | Average # of secondary neurospheres formed/well |
|---|---|
| PDGF | 0 |
| EGF | 3.12 ± 1.64 (n = 3) |

Therefore, the cells in PDGF-derived primary neurospheres cannot proliferate in response to PDGF. In contrast, these cells can proliferate and form secondary neurospheres in response to EGF.

Example 4

EGF-Derived Primary Neurospheres can be Subcultured into Either EGF- or PDGF-Containing Media To determine if the neurospheres derived in EGF-containing media have different proliferation properties as those of PDGF-generated neurospheres, primary EGF neurospheres were generated from embryonic day 14 striatum by culturing dissociated striatum in EGF (20 ng/ml) containing define culture media at a cell density of 200,000 cells/ml. Subsequently, individual neurospheres were isolated, placed in individual wells in either PDGF or EGF containing media, and dissociated mechanically. The numbers of secondary neurospheres that came from a single primary EGF-generated neurospheres are given below (eight wells for each condition; numbers indicate average number of secondary neurospheres/well):

|  | EGF-containing media | PDGF-containing media |
| --- | --- | --- |
| Exp. #1 | 27 | 21.5 |
| Exp. #2 | 14.1 | 26.7 |

Accordingly, EGF-derived neurospheres, in contrast to PDGF-derived neurospheres, contain cells which can proliferate in response to either EGF or PDGF to form secondary neurospheres. Clearly, the PDGF-derived neurospheres define a novel class of progenitor cells which are distinct from multipotent neural stem cells which give rise to the EGF-derived neurospheres.

Example 5

Primary PDGF-Derived Neurospheres Differentiate into Neurons and Oligodendrocytes Primary PDGF-derived spheres, derived either clonally (10,000 cells/ml) or in high density culture (200,000 cells/ml), were plated without dissociation onto poly-1-ornithine coated coverslips and allowed to differentiate for 2-5 days in vitro in the absence of serum. These PDGF derived spheres, whether produced clonally or in high density culture, yielded differentiated neurons and a smaller number of oligodendrocytes. No astrocytes could be detected. Again, these results indicate that the primary neurospheres formed in response to PDGF define a novel class of progenitor cells.

Example 6

The PDGF-Induced Neurospheres are Derived from Different Cells as the EGF-Induced Neurospheres In order to locate the cells that give rise to the novel progenitor cells described herein, we dissected ganglionic eminence to two portions. Thus, the ganglionic eminence was isolated from E14 embryos of mice, and the medial ganglionic eminence (MGE) was separated from the lateral ganglionic eminence (LGE). MGE and LGE were then dissociated and cultured as described in Example 1. The resulting primary culture was exposed to EGF or PDGF in addition to the defined culture media, and the number of neurospheres were counted and summarized below.

TABLE 2

Neurosphere formation using medial ganglionic eminence and lateral ganglionic eminence

| Source of brain tissue | PDGF | | EGF | |
| --- | --- | --- | --- | --- |
|  | MGE | LGE | MGE | LGE |
| Average number of neurospheres | 10.22 ± 1.11 | 1.27 ± 0.45 | 16.9 ± 2.87 | 9.64 ± 1.59 | n = 2 or 3

These results show that the PDGF-induced neurospheres are primarily derived from MGE. In contrast, the EGF-induced neurospheres can be produced efficiently using both MGE and LGE, and the MGE produces more spheres in response to EGF than LGE. Accordingly, it is highly unlikely that the same cell type give rise to both PDGF- and EGF-induced neurospheres. Instead, the cells that give rise to PDGF-induced neurospheres are located primarily in the MGE, while the cells that form EGF-induced spheres are located in both MGE and LGE.

Example 7

Combination of PDGF and EGF

We also tested the effect of combining PDGF and EGF on the number of neurospheres formed. Thus, brain tissue was prepared as described in Example 1 and cultured in the presence of PDGF, EGF, or the combination of PDGF and EGF. The number of neurospheres from each experiment was then counted and shown in Table 3.

TABLE 3

Combined effect of PDGF and EGF

|  | PDGF | EGF | PDGF + EGF |
| --- | --- | --- | --- |
| Average number of neurospheres | 73.36 ± 7.13 | 80.5 ± 8.57 | 137.75 ± 11.7 |

These results indicate that there is an additive effect when PDGF and EGF are combined. This additive effect is consistent with the notion that PDGF and EGF stimulate different cells to proliferate and form neurospheres.

We claim:

1. A method of making a neural progenitor cell population, comprising:
    (a) dissociating brain tissue
    (b) culturing the dissociated brain tissue of step (a) in the presence of platelet derived growth factor (PDGF) and in the absence of both EGF and FGF-2,
    whereby the neural progenitor cells proliferate and produce primary neurospheres.

2. The method of claim 1 wherein the brain tissue is obtained from an embryonic brain.

3. The method of claim 1 wherein the brain tissue is obtained from medial ganglionic eminence.

4. The method of claim 1 wherein the brain tissue is obtained from an adult brain.

5. A method of making a neural progenitor cell population, comprising:
    a) dissociating brain tissue that is harvested from a mammal; and
    b) culturing the dissociated brain tissue of step a) in the presence of platelet derived growth factor (PDGF) under conditions that allow proliferation of said progenitor cell and production of a primary neurosphere, wherein the dissociated brain tissue is not cultured in the presence of EGF, FGF-2, or TGF-α.

6. A method of differentiating a neural progenitor cell population comprising the steps of
    a) making a neural progenitor cell population according to the method of claim 1, wherein the neural progenitor cell population forms primary neurospheres;

b) plating the primary neurospheres of step (a) onto a coated surface; and c) differentiating the neurospheres of step b).

7. A method of differentiating a neural progenitor cell population comprising the steps of a) making a neural progenitor cell population according to the method of claim 5, wherein the neural progenitor cell population forms primary neurospheres;

b) plating the primary neurospheres of step (a) onto a coated surface; and c) differentiating the neurospheres of step b).

8. The method of claim 1, further comprising isolating the primary neurospheres.

9. The method of claim 5, further comprising isolating the primary neurosphere.

* * * * *